United States Patent
Ehmke et al.

(10) Patent No.: US 9,433,448 B2
(45) Date of Patent: Sep. 6, 2016

(54) NAIL-BASED COMPLIANT HIP FIXATION SYSTEM

(71) Applicant: ACUMED LLC, Hillsboro, OR (US)

(72) Inventors: Larry W. Ehmke, Beaverton, OR (US); Steven P. Horst, Dayton, OR (US); Mark B. Sommers, Beaverton, OR (US); Brian R. Conley, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 14/565,116

(22) Filed: Dec. 9, 2014

(65) Prior Publication Data

US 2015/0157369 A1     Jun. 11, 2015

Related U.S. Application Data (60) Provisional application No. 61/913,611, filed on Dec. 9, 2013.

(51) Int. Cl.
*A61B 17/56* (2006.01)
*A61B 17/72* (2006.01)
*A61B 17/74* (2006.01)

(52) U.S. Cl.
CPC ......... *A61B 17/7241* (2013.01); *A61B 17/744* (2013.01)

(58) Field of Classification Search
CPC   A61B 17/72; A61B 17/7241; A61B 17/746; A61B 17/744; A61B 17/725
USPC .................................... 606/62–68
See application file for complete search history.

(56) References Cited

U.S. PATENT DOCUMENTS

| | | |
|---|---|---|
| 2,699,774 A | 1/1955 | Livingston |
| 4,129,903 A | 12/1978 | Huggler |
| 4,399,813 A | 8/1983 | Barber |
| 4,657,001 A | 4/1987 | Fixel |
| 4,776,330 A | 10/1988 | Chapman et al. |
| 4,959,064 A | 9/1990 | Engelhardt |
| 5,032,125 A | 7/1991 | Durham et al. |

(Continued)

FOREIGN PATENT DOCUMENTS

WO        2008098728 A2     8/2008

OTHER PUBLICATIONS

Biomet Trauma, "VHS® Vari-Angle Hip System Surgical Technique" © 2008 Biomet, rev. Mar. 2008, 12 pages.

(Continued)

*Primary Examiner* — Mary Hoffman
*Assistant Examiner* — Tara R Carter
(74) *Attorney, Agent, or Firm* — Kolisch Hartwell, P.C.

(57) ABSTRACT

System, including methods, devices, and kits, for hip fixation. The system may comprise an intramedullary nail configured to be placed longitudinally into a proximal femur. The system also may comprise a fixation element configured to be placed transversely through the nail, such that the fixation element is slideable along its long axis in the nail and extends out of the nail to a head of the proximal femur and is anchored in the head. A compliant member may be located in the nail and configured to deform reversibly in response to a load applied to the head of the proximal femur after placement of the fixation element, to reversibly change an angular orientation of the fixation element with respect to the nail.

19 Claims, 6 Drawing Sheets

(56) References Cited

U.S. PATENT DOCUMENTS

| | | | |
|---|---|---|---|
| 5,041,116 A | 8/1991 | Wilson | |
| 5,098,434 A | 3/1992 | Serbousek | |
| 5,176,681 A | 1/1993 | Lawes et al. | |
| 5,578,035 A | 11/1996 | Lin | |
| 5,728,099 A | 3/1998 | Tellman et al. | |
| 5,743,912 A | 4/1998 | Lahille et al. | |
| 5,759,184 A | 6/1998 | Santangelo | |
| 6,106,528 A * | 8/2000 | Durham et al. | 606/64 |
| 6,238,126 B1 | 5/2001 | Dall | |
| 6,296,645 B1 | 10/2001 | Hover et al. | |
| 6,443,954 B1 | 9/2002 | Bramlet et al. | |
| 6,468,278 B1 | 10/2002 | Muckter | |
| 6,562,042 B2 | 5/2003 | Nelson | |
| 6,645,209 B2 | 11/2003 | Hall, IV et al. | |
| 6,648,889 B2 | 11/2003 | Bramlet et al. | |
| 6,695,844 B2 | 2/2004 | Bramlet et al. | |
| 6,783,530 B1 | 8/2004 | Levy | |
| 6,855,146 B2 | 2/2005 | Frigg et al. | |
| 7,041,104 B1 | 5/2006 | Cole et al. | |
| 7,135,023 B2 | 11/2006 | Watkins et al. | |
| 7,175,626 B2 | 2/2007 | Neff | |
| 7,503,919 B2 | 3/2009 | Shaw | |
| 7,569,055 B2 | 8/2009 | Zander et al. | |
| 7,591,819 B2 | 9/2009 | Zander et al. | |
| 7,763,023 B2 | 7/2010 | Gotfried | |
| 7,972,336 B2 | 7/2011 | James et al. | |
| 8,114,078 B2 | 2/2012 | Aschmann | |
| 8,137,348 B2 | 3/2012 | Gotfried | |
| 8,157,803 B1 | 4/2012 | Zirkle, Jr. et al. | |
| 8,158,802 B2 | 4/2012 | Lahm et al. | |
| 8,172,841 B2 | 5/2012 | Defossez | |
| 8,177,786 B2 | 5/2012 | Leyden et al. | |
| 8,241,287 B2 | 8/2012 | Prager et al. | |
| 8,252,059 B2 | 8/2012 | Overes et al. | |
| 8,287,540 B2 | 10/2012 | LeCronier et al. | |
| 8,398,636 B2 | 3/2013 | Simon et al. | |
| 8,414,582 B2 | 4/2013 | Overes et al. | |
| 8,617,227 B2 | 12/2013 | Succc et al. | |
| 8,790,343 B2 | 7/2014 | McClellan et al. | |
| 9,254,153 B2 | 2/2016 | Simon et al. | |
| 2002/0007185 A1 | 1/2002 | Aghion | |
| 2002/0032445 A1 | 3/2002 | Fujiwara | |
| 2002/0173792 A1 * | 11/2002 | Severns et al. | 606/62 |
| 2003/0074000 A1 | 4/2003 | Roth et al. | |
| 2004/0260290 A1 | 12/2004 | Zander et al. | |
| 2005/0010224 A1 | 1/2005 | Watkins et al. | |
| 2005/0055024 A1 | 3/2005 | James et al. | |
| 2005/0143739 A1 | 6/2005 | Shinjo et al. | |
| 2005/0203510 A1 | 9/2005 | Sohngen | |
| 2006/0095039 A1 | 5/2006 | Mutchler | |
| 2006/0149248 A1 | 7/2006 | Schlienger et al. | |
| 2006/0155281 A1 | 7/2006 | Kaup et al. | |
| 2006/0200160 A1 | 9/2006 | Border et al. | |
| 2006/0241604 A1 | 10/2006 | Frigg et al. | |
| 2006/0241606 A1 | 10/2006 | Vachtenberg et al. | |
| 2007/0100343 A1 | 5/2007 | Cole et al. | |
| 2007/0219636 A1 | 9/2007 | Thakkar | |
| 2007/0270847 A1 | 11/2007 | Shaw | |
| 2008/0140077 A1 | 6/2008 | Kebaish | |
| 2008/0177291 A1 | 7/2008 | Jensen et al. | |
| 2008/0183170 A1 | 7/2008 | Metzinger et al. | |
| 2008/0255559 A1 | 10/2008 | Leyden et al. | |
| 2008/0269752 A1 | 10/2008 | Simon et al. | |
| 2008/0281326 A1 | 11/2008 | Watanabe et al. | |
| 2009/0048600 A1 | 2/2009 | Matityahu et al. | |
| 2009/0048606 A1 | 2/2009 | Tipirneni et al. | |
| 2009/0088752 A1 * | 4/2009 | Metzinger et al. | 606/62 |
| 2009/0248025 A1 | 10/2009 | Haidukewych et al. | |
| 2009/0326534 A1 | 12/2009 | Yamazaki et al. | |
| 2010/0121327 A1 | 5/2010 | Velikov | |
| 2010/0179549 A1 | 7/2010 | Keller et al. | |
| 2010/0179551 A1 | 7/2010 | Keller et al. | |
| 2010/0249781 A1 | 9/2010 | Haidukewych et al. | |
| 2010/0249852 A1 | 9/2010 | Brumfield et al. | |
| 2010/0268285 A1 | 10/2010 | Tipirneni et al. | |
| 2010/0331843 A1 | 12/2010 | Grusin | |
| 2011/0196370 A1 * | 8/2011 | Mikhail | 606/62 |
| 2011/0295255 A1 | 12/2011 | Roberts et al. | |
| 2012/0109128 A1 | 5/2012 | Frigg | |
| 2012/0130370 A1 * | 5/2012 | Kinmon | 606/62 |
| 2012/0136356 A1 | 5/2012 | Doherty et al. | |
| 2012/0310289 A1 | 12/2012 | Bottlang et al. | |
| 2013/0041414 A1 | 2/2013 | Epperly et al. | |
| 2013/0204304 A1 | 8/2013 | Bottlang et al. | |
| 2014/0052132 A1 | 2/2014 | Matityahu et al. | |
| 2014/0058392 A1 | 2/2014 | Mueckter et al. | |
| 2014/0094802 A1 | 4/2014 | Simon et al. | |
| 2014/0135769 A1 | 5/2014 | Ziran | |
| 2014/0214035 A1 | 7/2014 | Simon | |
| 2014/0214098 A1 | 7/2014 | Probe et al. | |
| 2014/0330274 A1 | 11/2014 | Matityahu et al. | |
| 2015/0250507 A1 | 9/2015 | Harrison et al. | |
| 2016/0051295 A1 | 2/2016 | Nakamura et al. | |

OTHER PUBLICATIONS

Kwok Sui Leung, M.D. et al., "Gamma3 Trochanteric Nail 180" Operative Technique brochure, Stryker © 2011.

Amir Matityahu et al., "The Variable Angle Hip Fracture Nail Relative to the Gamma 3: A Finite Element Analysis Illustrating the Same Stiffness and Fatigue Characteristics", Hindawi Publishing Corporation, Advances in Orthopedics, vol. 2013, Article ID 143801, © 2013, 11 pages.

Blaine R. Copenheaver, Authorized Officer, U.S. Patent and Trademark Office, "International Search Report" in connection with related PCT Patent Application No. PCT/US2014/069367, dated Mar. 6, 2015, 2 pages.

Blaine R. Copenheaver, Authorized Officer, U.S. Patent and Trademark Office, "Written Opinion of the International Searching Authority" in connection with related PCT Patent Application No. PCT/US2014/069367, dated Mar. 6, 2015, 8 pages.

* cited by examiner

NAIL-BASED COMPLIANT HIP FIXATION SYSTEM

CROSS-REFERENCE TO PRIORITY APPLICATION

This application is based upon and claims the benefit under 35 U.S.C. §119(e) of U.S. Provisional Patent Application Ser. No. 61/913,611, filed Dec. 9, 2013, which is incorporated herein by reference in its entirety for all purposes.

INTRODUCTION

The hip joint is a synovial joint formed by articulation of the head of the femur and the acetabulum of the pelvis. The hip joint(s) supports the weight of the body when a person is standing, walking, or running, among others.

Trauma to the femur can fracture the proximal femur near the hip joint. Depending on the position and severity of fracture, the femoral head may be replaced with a prosthesis, or the bone may be stabilized with an implanted fixation device to hold the femoral head in position while the femur heals.

A nail-based fixation device involving an intramedullary nail and a screw is commonly utilized for fixation. The nail is placed axially into the proximal femur from a proximal end thereof. Then, the screw is inserted obliquely into the proximal femur from a lateral side thereof, through the nail and the femoral neck, and into the femoral head. The screw may be placed at an angle of about 125 degrees with respect to the nail, to account for the angle between the femoral head/neck and the femoral shaft. The screw and the nail both generally span the fracture. Accordingly, the screw can transfer the load from the femoral head to the nail, which can stabilize the fractured femur more effectively and improve healing.

The screw may not be fixed with respect to the nail. Instead, the screw may be permitted to slide parallel to its long axis in an aperture defined by the nail. More particularly, the screw may be allowed to migrate laterally (anatomically) after installation, for dynamic compression of the fracture, which can encourage and improve fracture healing.

The ability of the screw to migrate can improve performance dramatically. However, the fixation device does not always provide a successful outcome. In some cases, the femoral head is damaged by cut-out, where migration of the femoral head relative to the screw causes the screw to project through the articular surface of the femoral head, and/or to split the femoral head.

An improved nail-based hip fixation system is needed.

SUMMARY

The present disclosure provides a system, including methods, devices, and kits, for hip fixation. The system may comprise an intramedullary nail configured to be placed longitudinally into a proximal femur. The system also may comprise a fixation element configured to be placed transversely through the nail, such that the fixation element is slideable along its long axis in the nail and extends out of the nail to a head of the proximal femur and is anchored in the head. A compliant member may be located in the nail and configured to deform reversibly in response to a load applied to the head of the proximal femur after placement of the fixation element, to reversibly change an angular orientation of the fixation element with respect to the nail.

DETAILED DESCRIPTION

The present disclosure provides a system, including methods, devices, and kits, for hip fixation. The system may comprise an intramedullary nail configured to be placed longitudinally into a proximal femur. The system also may comprise a fixation element configured to be placed transversely through the nail, such that the fixation element is slideable along its long axis in the nail and extends out of the nail to a head of the proximal femur and is anchored in the head. A compliant member may be located in the nail and configured to deform reversibly in response to a load applied to the head of the proximal femur after placement of the fixation element, to reversibly change an angular orientation of the fixation element with respect to the nail.

The hip fixation system of the present disclosure may have a reduced stiffness (greater compliance), to reduce the peak loads created at the implant-bone interface (in the femoral head), thereby reducing the propensity for microcrack formation, which can ultimately lead to cut-out of the implant through the femoral head. Accordingly, the hip fixation system may have various advantages over existing hip fixation systems including a lower incidence of cut-out through the femoral head, improved patient comfort, better force dampening, less swarf created through wear, and/or the like.

Further aspects of the present disclosure are described in the following sections: (I) overview of nail-based, compliant hip fixation systems, (II) methods of bone fixation, (III) composition of system components, (IV) kits, and (V) examples.

I. Overview of Nail-based, Compliant Hip Fixation Systems

This section describes exemplary nail-based hip fixation systems having a slideable fixation element, such as a screw, extending out of an intramedullary nail and angularly oriented with respect to the nail by a compliant interface.

Figure 1:
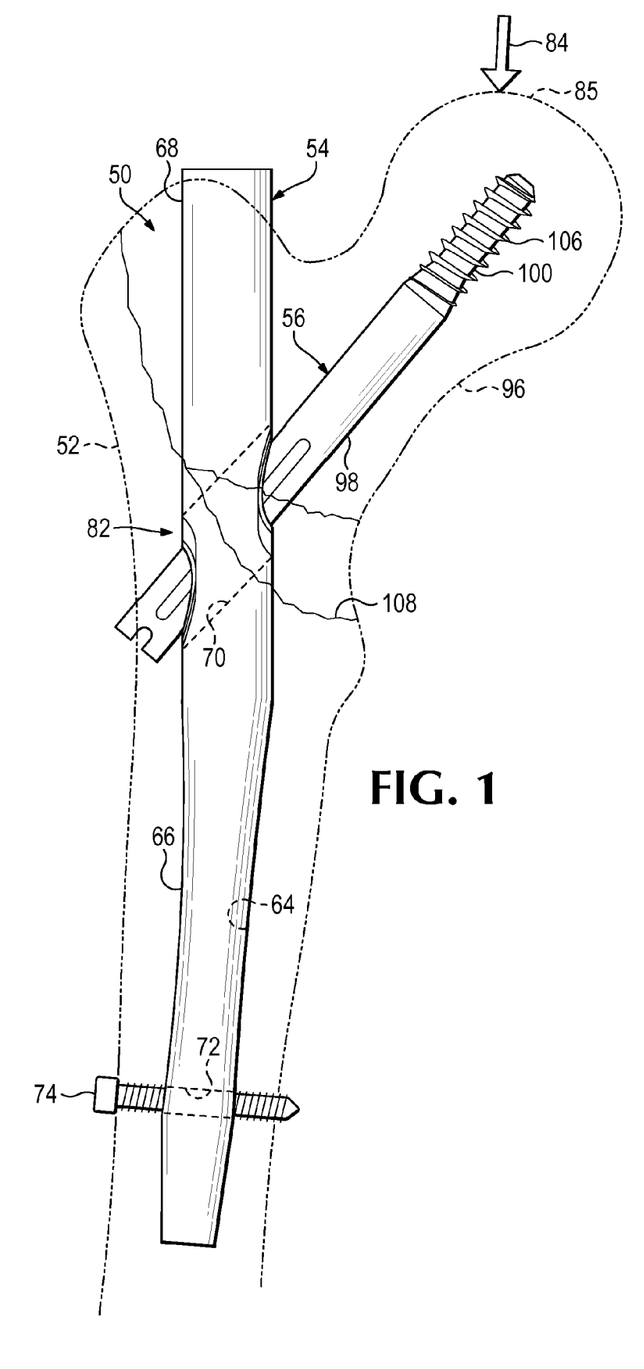
FIG. 1 is a front view of selected aspects of an exemplary compliant hip fixation system installed in a fractured proximal femur and including an intramedullary nail and a fixation element extending obliquely and slideably through the nail, with the nail containing a compliant member including an elastomer, in accordance with aspects of the present disclosure.
Figures 2, 3:
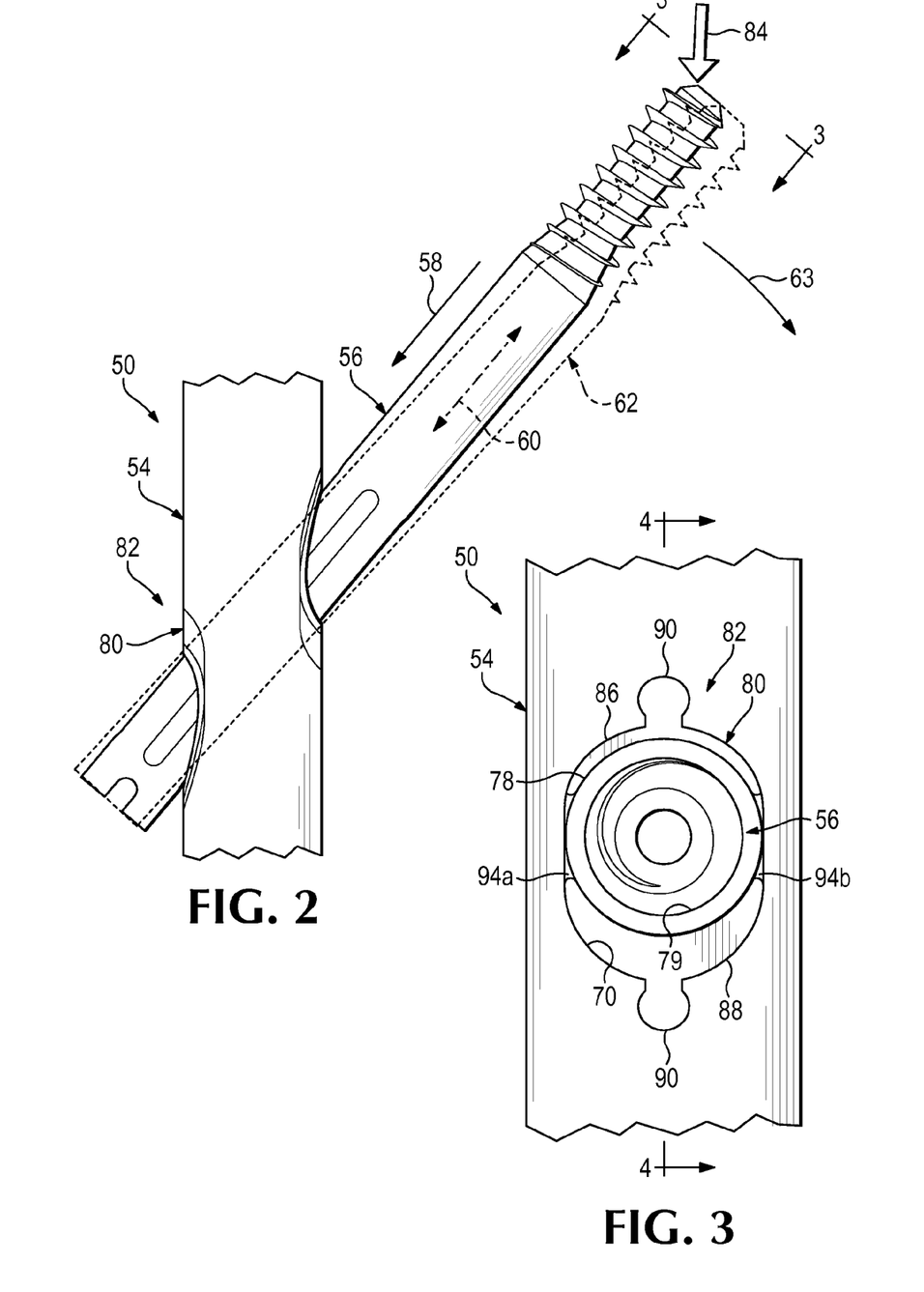
FIG. 2 is a fragmentary front view of the hip fixation system of FIG. 1, taken in the absence of the proximal femur and showing angular motion of the fixation element with respect to the nail in phantom outline.
FIG. 3 is fragmentary view of the hip fixation system of FIG. 1, taken generally along line 3-3 of FIG. 2 such that the system is viewed along the slideable fixation element from a leading end thereof.
Figure 4:
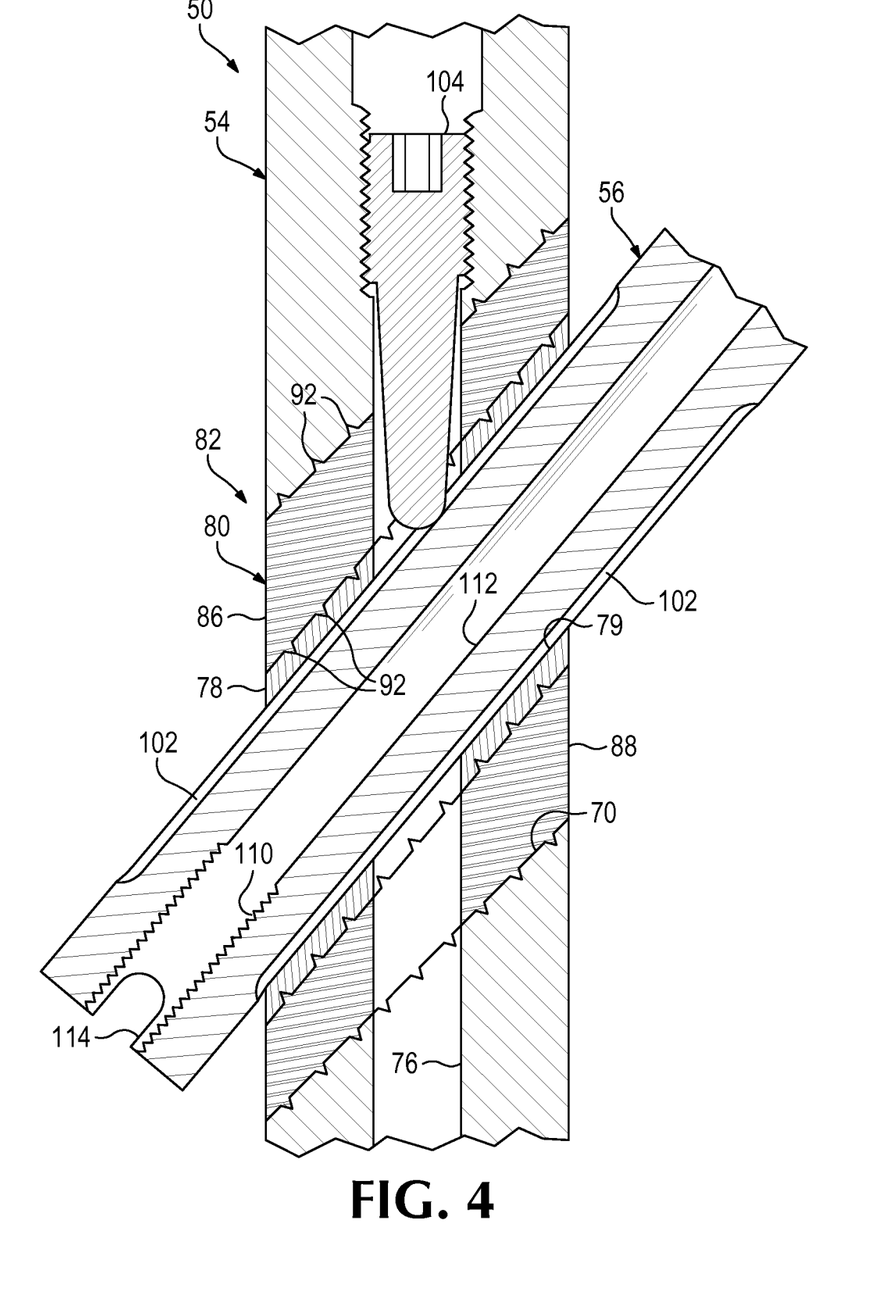
FIG. 4 is a fragmentary sectional view of the hip fixation system of FIG. 1, taken generally along line 4-4 of FIG. 3 through a central plane of the system.

FIGS. 1-4 show various views of an exemplary hip fixation system 50 installed in a fractured proximal femur 52 (FIG. 1) or in the absence of the femur (FIGS. 2-4). System 50 (interchangeably termed an implant or a device) may include an intramedullary nail 54 intersected by a slideable fixation element 56 (interchangeably termed a fastener). Fixation element 56 is slideable, indicated by a motion arrow at 58, relative to the nail on an axis 60 (see FIG. 2). The axis may be coaxial to the central long axis of the fixation element and may be movable, as described in more detail below, to change an angular orientation of the fixation element with respect to the nail, indicated in phantom outline at 62 and by a motion arrow at 63. The fixation element may retain the ability to slide along its long axis as its angular orientation varies. In some embodiments, the fixation element may not be slideable in the nail after the fixation system is fully installed in the femur. In some embodiments, the fixation element may be slideable in both directions parallel to the long axis of the fixation element. In some embodiments, the fixation element may be slideable laterally and not medially along the long axis of the fixation element.

Nail 54 may be configured to be placed into a medullary canal 64 of proximal femur 52 from a proximal end thereof (see FIG. 1). The end of the nail may be flush, recessed, or protruding after placement into the proximal femur. The nail may have a leading region 66 projecting from a trailing region 68. The leading region may have a smaller average diameter than the trailing region and may be described as a stem or shaft, and the trailing region as a head. The nail may taper toward the leading region and/or the leading boundary of the nail. The nail may be linear such that leading and trailing regions 66, 68 are coaxial. Alternatively, the nail may have a longitudinal bend, as shown, such that the leading and trailing regions are angularly offset from one another by at least about 1, 2, 4, or 6 degrees, among others.

The nail may define one or more transverse apertures 70, 72 that extend transversely (orthogonally or obliquely) through the nail, such as between opposite side wall regions of the nail. Each aperture may be a locking (e.g., threaded) or nonlocking aperture. Proximal aperture 70 may be defined by trailing region 68 of the nail. The proximal aperture may be sized to receive and surround a region of fixation element 56, with the fixation element extending through the aperture. The proximal aperture may be partially filled or occupied before the fixation element is placed into the proximal aperture, as described below.

The nail also may define one or more distal transverse apertures 72 to receive at least one other fastener, such as a bone screw 74, that attaches leading region 66 of the nail to a shaft region of the femur. The nail further may define an axial bore 76 that extends into the nail from the nail's trailing boundary (see FIG. 4). Axial bore 76 may extend along any suitable portion of the length of the nail, such as only into the trailing region, through the trailing region and into the leading region but not completely through the nail, or through the entire length of the nail. In some embodiments, the nail may define two or more proximal apertures to receive two or more proximal fixation elements 56.

Proximal aperture 70 (and/or fixation element 56) may extend through nail 54 transversely, at an oblique angle relative to the nail, such as at an obtuse angle of greater than about 110 degrees or about 110-150, 120-140, or 120-130 degrees, among others. The proximal aperture may or may not be cylindrical and may or may not vary in diameter along the aperture.

The wall of the proximal aperture may or may not be configured to contact the fixation element. For example, at least one bearing member, such as a sleeve 78 (interchangeably termed a bushing), may be positioned and/or mounted in the aperture (see FIGS. 3 and 4). The sleeve may contact the fixation element while permitting the fixation element to slide in the nail. The sleeve may maintain separation between nail 54 and fixation element 56. The sleeve may define a channel 79 that is slightly larger than the diameter of the shaft of the fixation element, to allow the fixation element to slide in channel 79 without any substantial change in the angular orientation of the fixation element with respect to the sleeve.

A compliant member 80 may be located at least partially in nail 54, inside transverse aperture 70 (see FIGS. 2-4), and may be discrete from fixation element 56. The compliant member alternatively may be described as a biasing member or a deformable member. Compliant member 80 forms at least part of a compliant interface 82 (which may be described as a deformable and/or biasing interface) that permits angular motion of fixation element 56 with respect to nail 54, indicated at 62 and 63 in FIG. 2. For example, a downward force or load 84 applied to the end of fixation element 56 via bone, such as when a subject (the implant recipient) is standing or walking, applies a torque to fixation element 56. The torque may cause deformation of compliant member 80 and an accompanying change in the angular orientation of the fixation element. Deformation of the compliant member may absorb some of the load applied to the hip joint and may help to govern and cushion load transfer during use of the hip joint (such as when walking). Fixation element 56 may change its angular orientation in a varus direction, indicated at 62, in response to load 84 (se FIG. 2). The attached femoral head 85 can move with the fixation element, producing varus travel of the femoral head, which may reduce the tendency of the fixation element to move relative to the femoral head.

Changes to the angular orientation of the fixation element may be dynamic as the subject moves. For example, these changes may be cyclical when the subject walks. The fixation element may move toward a more perpendicular orientation when load 84 is applied (i.e., when the associated femur is bearing the weight of the subject) and may move back to a more oblique orientation when load 84 is removed (e.g., when the contralateral femur is bearing the weight of the subject).

Compliant interface 82 may permit fixation element 56 to change its angular orientation with respect to nail 54 by any suitable amount from a relatively neutral or unloaded ("home") configuration during normal use, such as less than about 5 or 2 degrees, and/or at least about 0.2, 0.5, or 1 degree, among others. The end of the fixation element farthest from the nail may have a maximum range of motion from the neutral or unloaded configuration during normal use of less than about 5 mm or 2 mm, or greater than about 0.5 mm or 1 mm, among others.

The compliant member (and/or compliant interface) is resilient (interchangeably termed elastic), meaning that the compliant member (and/or compliant interface) is capable of recovering its previous shape and size after being deformed (i.e., after a deforming force/load is removed). The resiliency of the compliant member (and/or compliant interface) stores energy and then uses the stored energy to urge the fixation element back toward a neutral/unloaded position or orientation when the load is reduced or removed. The compliant member may be viscoelastic. In some embodiments, the compliant member may be described as a spring. The compliant member can act as a mechanical damper, which may absorb energy to function as a cushion, particularly to absorb sudden impacts produced by standing up, walking, running, etc.

In some embodiments, the compliant member may provide non-linear load resistance/absorption. For example, as the compliant member is deformed, further deformation may be progressively more difficult and the load needed for further deformation may increase non-linearly. The compliant member may be formed of a single material or may be a composite of two or more materials, such as metal and polymer, to provide optimal dampening.

Compliant member 80 may have any suitable location and structure. The compliant member may be at least partially contained by the nail and thus may be disposed at least partially or completely inside nail 54 and/or within a transverse aperture thereof. Locating the compliant member completely within the nail before nail installation may facilitate advancing the nail into the femur without interference from any protruding portion of the fixation element. The compliant member may be disposed at least partially or predominantly inferior to (below) the fixation element, at least partially or predominantly superior to (above) the fixation element, or both, among others. Accordingly, the compliant member may bracket a shaft portion of the fixation element and/or may surround the shaft portion.

The compliant member, or at least a portion thereof, may be discrete from or continuous with the nail. The compliant member may include only a single deformable element or two or more discrete deformable elements, such as upper and lower deformable elements 86, 88 that collectively form the compliant member (see FIGS. 3 and 4). For example, in the depicted embodiment, elements 86 and 88 are disposed respectively superior and inferior to fixation element 56 (i.e., the elements collectively bracket a portion of fixation element from above and below). The compliant member and/or each deformable element may form a projecting key 90 that is received in a complementary recess defined by the nail, or vice versa, to restrict motion of the compliant member with respect to the nail. Alternatively, or in addition, abutted surfaces of sleeve 78 and compliant member 80, and/or abutted surfaces of compliant member 80 and an interior wall of nail 54 (formed by transverse aperture 70) may have complementary surface features 92, namely, projections (e.g., barbs/ridges) and corresponding indentations or recesses (e.g., grooves). The complementary surface features may restrict translational and/or rotational movement of sleeve 78, compliant member 80, and/or nail 54 relative to one another.

Compliant member 80 may provide radially uniform or radially nonuniform resistance to angular motion (and/or radially uniform or radially nonuniform ranges of angular motion) of fixation element 56 with respect to nail 54. For example, in the depicted embodiment, compliant member 80 is not symmetrically positioned around fixation element 56 (see FIG. 3). The compliant member may not completely surround any portion of fixation element 56, as shown, or may extend completely around the fixation element at one or more positions along the fixation element. Also, the thickness of the compliant member may (or may not) vary around and/or along the fixation element. In FIG. 3, compliant member 80 is positioned above and below the sleeve and fixation element, but not substantially on opposite sides of the sleeve and fixation element, which causes angular motion of the fixation element to be constrained substantially to one plane of a set of three mutually orthogonal planes (here, a vertical plane defined by the long axes of nail 54 and fixation element 56). The compliant member also may have a thickness that varies along the sleeve. For example, in the depicted embodiment, the compliant member is thicker below relative to above the fixation element near the medial side of the nail, but this relationship is reversed near the lateral side of the nail (see FIGS. 3 and 4). Accordingly, the compliant member may provide differential resistance to angular motion of the fixation element in opposite rotational directions in a plane, as shown, or may offer an equal resistance in both rotational directions.

In some embodiments, angular motion of the fixation element may be substantially restricted to a frontal plane, such that anterior/posterior motion of the fixation element is less than motion in the frontal plane. However, the system may be designed to permit any suitable amount of anterior/posterior motion of the fixation element.

The fixation element may change its angular orientation about a pivot axis or center of rotation, which may be fixed or movable with respect to the fixation element and/or nail as the angular orientation changes. The pivot axis or center of rotation may be inside or outside the nail.

In the depicted embodiment, fixation element 56 has a greater range of angular motion in a first plane defined collectively by nail 54 and fixation element 56, relative to a second plane orthogonal to the first plane and containing the long axis of fixation element 56. Also, resistance to angular motion, and/or the range of angular motion, of fixation element 56 in the first plane may be different in opposite rotational directions (clockwise (varus for the securing portion of the fixation element) and counterclockwise (valgus for the securing portion of the fixation element) in FIG. 2), from the neutral or unloaded (home) position of the fixation element. The resistance to moving the fixation element to a more orthogonal orientation with respect to the nail (clockwise in FIG. 2) may be less than the resistance to moving the fixation element to a less orthogonal orientation with respect to the nail (counterclockwise in FIG. 2), from an unloaded orientation, or vice versa.

Compliant member 80 and/or each deformable element 86, 88 thereof may have any suitable properties. The compliant member may, for example, be formed of a polymer, and may be described as an elastomeric member. The compliant member may be formed in situ (e.g., in proximal aperture 70 of the nail and/or around sleeve 78) or may be formed separately from the nail (and/or the sleeve) and then placed into the nail (and/or around the sleeve) after formation (e.g., during nail manufacture or during a surgical procedure to install the fixation system). The deformable elements collectively may extend incompletely around sleeve 78 to form a pair of gaps 94a, 94b disposed respectively forward and rearward of fixation element 56 after fixation system 50 is installed in the femur (i.e., respectively closer to the anterior and posterior sides of the nail). Alternatively, compliant member 80 may surround the fixation element circumferentially.

The wall thickness of the compliant member may be uniform or may vary. For example, in the depicted embodiment, deformable elements 86, 88 each taper between opposite ends of aperture 70. Upper deformable element 86 tapers toward an anatomically medial side of the nail (after installation) and lower deformable element 88 tapers in the opposite direction, namely, toward an anatomically lateral side of the nail (after installation).

Fixation element 56 may be configured to be disposed partially and slideably in nail 54 and to extend out the medial side of the nail, through femoral neck 96 and into femoral head 85, for anchorage therein (see FIG. 1). The fixation element may have a shaft 98, and a bone-securing portion 100 extending medially from the leading end of the shaft. Shaft 98 may be configured to slide parallel to the shaft's long axis inside the nail at various angular orientations of the shaft produced by deformation of compliant interface 82. The shaft may be a single piece, or two or more pieces, which may be assembled inside or outside the femur. The shaft may be at least generally cylindrical. The shaft may be shaped to prevent the fixation element from turning about the fixation element's long axis once the shaft is disposed in the nail and/or a sleeve therein. For example, the shaft may have one or more flats, grooves 102, and/or ridges, among others, extending along the shaft that engage a corresponding or complementary region defined by proximal aperture 70 or sleeve 78 therein.

Grooves 102 (or ridges) of the fixation element also or alternatively may be engaged by an anti-rotation element, such as a set screw 104, connected to nail 54 (see FIG. 4) and configured to prevent the fixation element from turning about its long axis. The set screw may be in threaded engagement with the nail and advanceable axially in the nail such that a leading end region of the set screw projects into one of grooves 102 of fixation element 56. The set screw may permit the fixation element to slide along its long axis both laterally and medially, or may restrict sliding medially (or both medially and laterally). The set screw also may restrict changes to the angular orientation of the fixation element, with respect to the nail, from occurring independently of changes to the deformation of the compliant member. In some embodiments, the set screw may have a leading end region that is axially biased, such as via a spring, with respect to and in an axial direction away from its trailing end region. With this arrangement, the leading end region of the set screw is biased to remain in one of grooves 102 as the fixation element changes its angular orientation with respect to the nail.

Bone-securing portion 100 may (or may not) be wider than shaft 98 of fixation element 56, to form one or more anchoring features to anchor the fixation element in the femoral head. In the depicted embodiment, bone-securing portion 100 defines an external thread 106 that attaches the bone-securing portion to femoral head 85 (see FIG. 1). Accordingly, the fixation element may be a screw. In other embodiments, bone-securing portion 100 may define one or more blades, flanges, spikes, deployable talons, etc., or any combination thereof, among others, to provide anchorage in the femoral head.

Fixation element 56 may have any other suitable structure. The fixation element may be configured to apply compression to the femur, such as across at least one fracture 108 spanned by fixation element 56 and nail 54 (see FIG. 1). The fixation element may define an internal thread 110 for attachment to a compression screw and/or a driver, and/or axial bore 112 extending through the fixation element (see FIG. 4). The fixation element also may define an internal and/or external driver-engagement structure 114 for engagement by a driver that turns or otherwise urges the fixation element into bone. The driver-engagement structure may, for example, be at least one slot, a socket (e.g., a hexagonal socket), external flats (e.g., a hexagonal, faceted perimeter), etc.

Further aspects of fixation systems for the proximal femur and/or other bones, which may be suitable for hip fixation system 50, are described elsewhere herein, such as in Section V, and in U.S. Provisional Patent Application Ser. No. 61/913,611, filed Dec. 9, 2013, which is incorporated herein by reference.

II. Methods of Bone Fixation

This section describes exemplary methods of bone fixation using any of the devices disclosed herein. The method steps described in this section may be performed in any suitable order and combination and may be combined with any other steps or device features disclosed elsewhere herein.

A bone to be fixed may be selected. The bone may be a femur or a humerus, among others. The bone may have at least one discontinuity, such as at least one fracture. The discontinuity may be disposed in a proximal region of the bone. For example, the discontinuity may be disposed generally between the shaft and the head of the bone. In some embodiments, the bone may be a fractured proximal femur having at least one fracture intersecting the neck, intertrochanteric, and/or pertrochanteric region(s) of the femur. Accordingly, the fracture(s) may intersect the femoral neck, the greater trochanter, the lesser trochanter, the shaft, or a combination thereof.

The bone may be prepared for receiving at least a portion of a fixation implant (interchangeably termed a fixation construct). For example, one or more holes may be drilled in the bone to receive the fixation element and other fasteners. Also, the medullary canal may be accessed and widened, if necessary, to receive the nail. Furthermore, pieces of the bone may be moved relative to another to reduce the fracture(s). One or more incisions through skin and other overlying soft tissue may be created to access the bone.

A nail may be selected for placement axially into the bone. The nail may be selected based on the size of the fixation element, the size and condition of the bone (e.g., the position and number of fractures or other discontinuities), and/or the like.

The nail may be attached to bone with one or more fasteners, such as bone screws. The nail may be arranged longitudinally in the bone.

The bone-securing portion of a fixation element may be placed into the head of the bone. For example, the bone-securing portion may be driven into the head by application of torque (i.e., by turning the bone-securing portion), percussive force (e.g., striking a portion of the fixation element), or a combination thereof, among others. The bone-securing portion and the shaft of the fixation element may be placed into the bone as a unit, or at least part of the shaft may be placed into the bone after the bone-securing portion has been installed in bone.

A portion of a fixation element may be placed in an aperture of the nail. The fixation element and the aperture may be arranged at least generally coaxial to one another, with the shaft of the fixation element extending out a medial side of the nail. Placement of a portion of the fixation element in the nail's aperture may be performed before, during, and/or after a securing portion of the fixation element is placed into the head of the bone. In exemplary embodiments, the securing portion of the fixation element is passed through an aperture of the nail and into the head of the proximal femur, after the nail has been placed into the femur and, optionally, secured to the femur.

A compliant member may be selected to form at least part of a compliant interface between the nail and the fixation element. The compliant member may be pre-assembled or pre-formed with the nail (i.e., during manufacture), such that selection of the nail also selects the compliant member. Alternatively, the compliant member (or at least one deformable element thereof) may be operatively associated with the nail/fixation element after manufacture, such as in the operating room by a surgeon or supporting personnel.

The compliant member may be selected peri-operatively based on one or more characteristics of the subject (the implant recipient), such as according to the subject's weight, age, health, fitness level, activity level, or a combination thereof, among others. Selection of a subject-specific compliant member may modulate load dampening in a subject-appropriate manner and/or may optimize the amount of micromotion at the fracture site(s) needed by the subject for efficient healing. The compliant member, if a removable/interchangeable component(s), may be assembled with the nail and/or the fixation element at any suitable time. Accordingly, selecting the compliant member may include selecting a compliant member and/or a deformable element thereof for insertion into the nail and/or may include selecting a nail already containing a suitable compliant member from a set of nails containing different compliant members (e.g., with different resistance to deformation).

The incision(s) may be closed over the implant. The implant may be left in place permanently or may be removed after the bone has healed.

III. Composition of System Components

This section describes exemplary materials for construction of components of the hip fixation system.

The nail, the fixation element (and/or other fasteners), and the compliant member/compliant interface may be formed of any suitable biocompatible material(s). Exemplary biocompatible materials that may be suitable for the nail, fixation element, and/or compliant member (and or a deformable element thereof) include (1) metal (for example, titanium or titanium alloys, alloys with cobalt and chromium (cobalt-chrome), stainless steel, etc.); (2) plastic/polymer (for example, ultra-high molecular weight polyethylene (UHMWPE), thermoplastic polyurethane (TPU), polymethylmethacrylate (PMMA), polytetrafluoroethylene (PTFE), polyetheretherketone (PEEK), nylon, polypropylene, and/or PMMA/polyhydroxyethylmethacrylate (PHEMA)); (3) composites (e.g., a polymer matrix (such as PEEK) containing carbon fibers and/or ceramic); (4) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, other bioresorbable polyesters, etc.; and/or the like.

In exemplary embodiments, the nail is formed of metal; all or part of the fixation element is formed of metal; and the compliant member/compliant interface is formed of metal (e.g., spring steel), polymer (e.g., an elastomer (such as thermoplastic polyurethane)), or a combination thereof. In some embodiments, a compliant member/compliant interface may, for example, include a metal portion (e.g., a core or base) and a polymer portion (e.g., a coating disposed on the metal portion). The polymer portion may be attached to the metal portion during formation (such as by overmolding the polymer portion onto the metal portion and/or molding the polymer portion between the metal portion and a nail) or after formation (such as with an adhesive, bonding, etc.).

IV. Kits

The fixation system may be provided as a system or kit with two or more different options for at least one of the components. For example, the system/kit may include two or more nails of different size and/or shape, two or more fixation elements of different size (e.g., different lengths/diameters) and/or shape, and/or two or more compliant members of different deformability (e.g., different flexibility/stiffness, range of motion, relative deformability in a pair of orthogonal planes, etc.). The two or more compliant members may be insertable into a nail or may be pre-attached to respective nails, such that the nails form a set having compliant members with distinguishable deformabilities relative to one another.

V. Examples

The following examples describe selected aspects and embodiments of the present disclosure including exemplary hip fixation devices and methods of installing the devices to fix a proximal femur. The components, aspects, and features of the devices described in each of these examples may be combined with one another and with the devices described above, in any suitable combination. These examples are intended for illustration and should not limit the entire scope of the present disclosure.

Example 1. Hip Fixation System With a Flexibly Mounted Sleeve

Figures 5, 6:
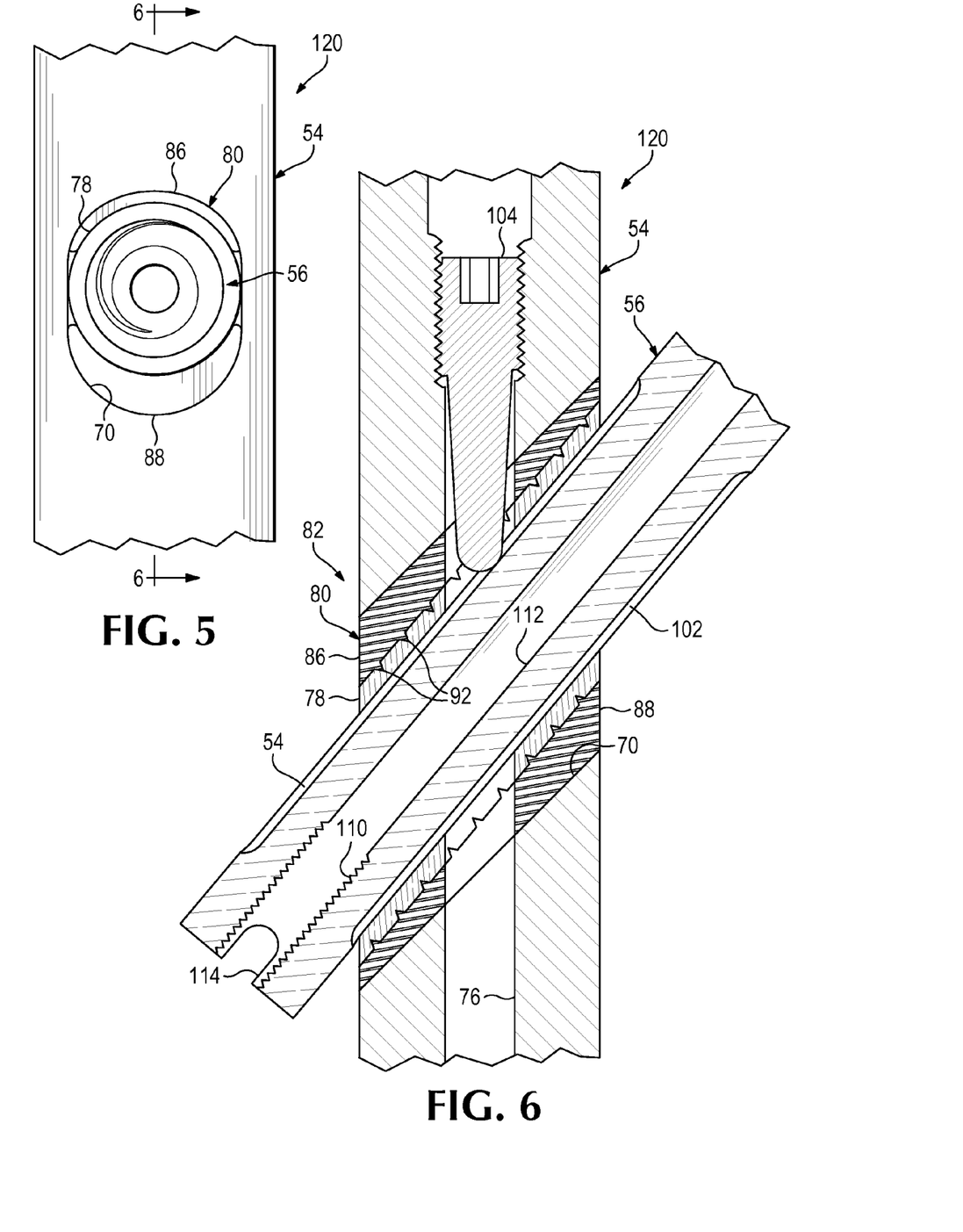
FIG. 5 is a fragmentary view, taken generally as in FIG. 3, of another exemplary compliant hip fixation system including an intramedullary nail and a slideable fixation element, with the nail containing a compliant member including an elastomer, in accordance with aspects of the present disclosure.
FIG. 6 is fragmentary sectional view of the fixation system of FIG. 5, taken generally along line 6-6 of FIG. 5 through a central plane of the system.

This example describes an exemplary hip fixation system 120 having a bearing member structured as a sleeve 78, mounted in a nail 54 via a compliant member 80, and surrounding a portion of a sliding fixation element 56; see FIGS. 5 and 6.

System 120 may have any suitable combination of the elements and features described above for fixation system 50 (see FIGS. 1-4). For example, sleeve 78 may be mounted in proximal aperture 70 of nail 54 via a pair of deformable elements 86, 88 disposed respectively above and below the sleeve. Complementary surface features 92 at the interface between sleeve 78 and deformable elements 86, 88 may restrict slippage of the sleeve with respect to the deformable elements. In contrast to system 50 (e.g., see FIG. 4), the complementary surface features may be absent from the interface between deformable elements 86, 88 and the wall of transverse aperture 70, which may allow the deformable elements to be inserted into aperture 70 after their formation. Lower deformable element 88 may be thicker than upper deformable element 86 on a medial side of the nail and thinner than the upper deformable element on a lateral side of the nail. In other embodiments, deformable elements 86, 88 may be formed integrally with one another. In other embodiments, surface features 92 may be absent from the interface between sleeve 78 and deformable elements 86, 88.

Sleeve 78 may, for example, be formed of metal and/or a hard plastic, to facilitate sliding of fixation element 56 axially. The sleeve may be configured to be contained completely within proximal aperture 70 of the nail or may project outside the nail. The sleeve may have a uniform wall thickness or the wall thickness may vary, such as to impart flexibility to the sleeve and to improve retention of the sleeve within the nail. In some embodiments, the sleeve may be narrower at a longitudinally middle portion thereof to prevent slippage of the sleeve out of the nail.

Example 2. Hip Fixation System With a Spring Contained by a Nail

Figure 7:
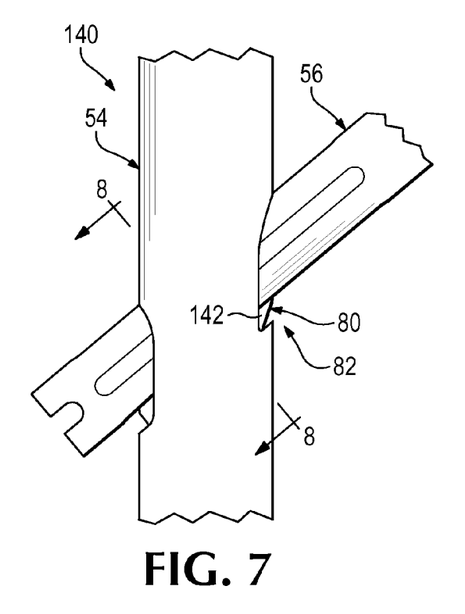
FIG. 7 is a fragmentary front view of another exemplary compliant hip fixation system including an intramedullary nail and a slideable fixation element, with the nail containing a compliant member structured as a bow spring, in accordance with aspects of the present disclosure.
Figure 8:
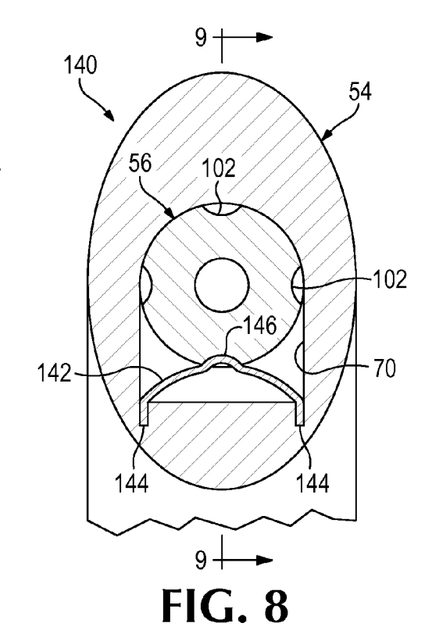
FIG. 8 is a fragmentary sectional view of the hip fixation system of FIG. 7, taken generally along line 8-8 of FIG. 7 through the bow spring.
Figure 9:
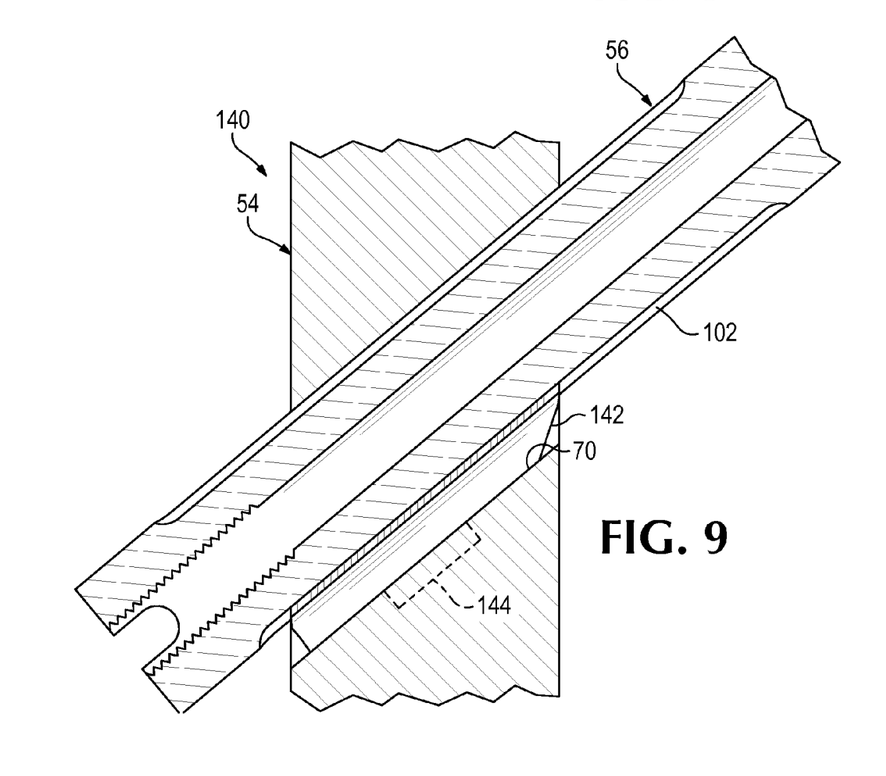
FIG. 9 is fragmentary sectional view of the fixation system of FIG. 7, taken generally along line 9-9 of FIG. 8 through the bow spring.

This example describes an exemplary hip fixation system 140 including a nail 54 that contains a compliant interface 82 including a compliant member 80 formed as a spring 142; see FIGS. 7-9.

Hip fixation system 140 may have any suitable combination of the elements and features described above for hip fixation systems 50 and 120 (see FIGS. 1-6). However, hip fixation system 140 may utilize spring 142 instead of deformable elements 86, 88, and sleeve 78 may be omitted (compare FIGS. 8 and 9 with FIGS. 3 and 4). Accordingly, fixation element 56 may be positioned in slideable contact with an inner wall of aperture 70 (see FIGS. 8 and 9).

Spring 142 may be located below fixation element 56. The spring may have one or more tabs 144 that are received in recesses (e.g., slots) defined in the wall of aperture 70, to retain the spring within the aperture. The spring may be supported by the nail at spaced positions, to create a bow spring (also called a beam spring). The spring may contact fixation element 56 at a central position of the spring that is generally intermediate the spaced positions. For example, the spring may define a ridge 146 that is received in an axial groove 102 defined by the shaft of fixation element 56, to prevent the fixation element from turning about its long axis after installation.

Example 3. Hip Fixation System with Threaded Insert for a Nail

This example describes an exemplary hip fixation system including a nail 54 that receives a discrete insert providing a sleeve to receive a portion of a fixation element 56.

The insert may be disposed in proximal aperture 70 of nail 54 and attached to the nail, such as with threaded engagement between an external thread of the insert and an internal thread defined by aperture 70. Fixation element 56 may extend slideably in the aperture of the insert. The insert may include or hold a compliant member to create a compliant interface. The compliant member may be formed separately from or integrally with a body of the insert. Further aspects of a threaded insert that may be suitable are described in U.S. Provisional Patent Application Ser. No. 61/913,611, filed Dec. 9, 2013, which is incorporated herein by reference.

Example 4. Nail With Integral Sleeve

This example describes exemplary hip fixation systems including a nail 54 containing a sleeve 78 formed integrally with the nail and sized for receiving a fixation element 56; see FIGS. 10-14. The fixation systems of this example may include any suitable combination of elements and features described above for fixation systems 50, 120, and/or 140.

Figure 10:
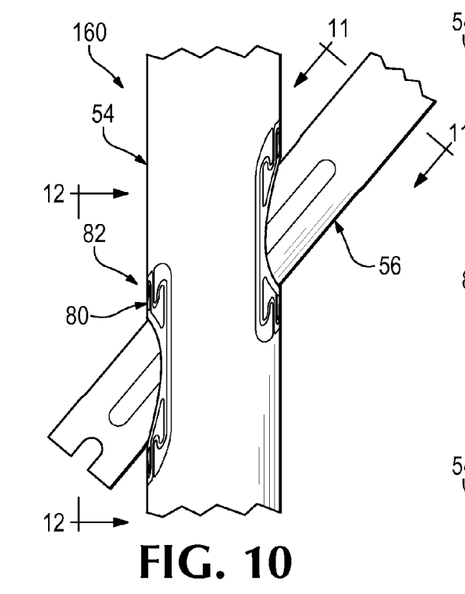
FIG. 10 is a fragmentary front view of still another exemplary compliant hip fixation system including an intramedullary nail and a slideable fixation element, with the nail containing a compliant member and a sleeve each formed integrally with the nail, in accordance with aspects of the present disclosure.
Figure 11:
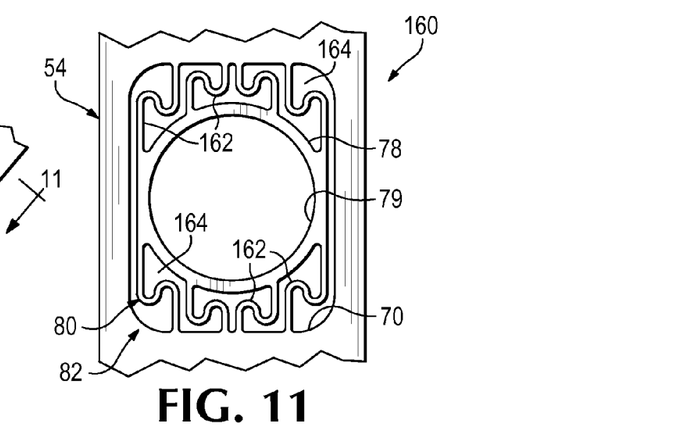
FIG. 11 is a fragmentary side view of the hip fixation system of FIG. 10, taken generally along line 11-11 of FIG. 10 in the absence of the slideable fixation element.
Figure 12:
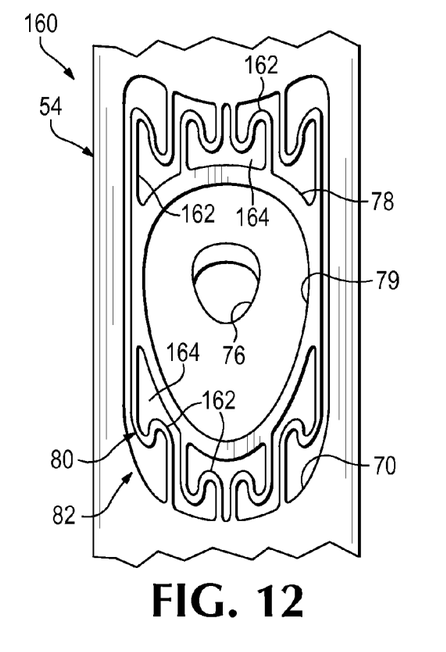
FIG. 12 is a fragmentary elevation view of the hip fixation system of FIG. 10, taken generally along line 12-12 of FIG. 10 in the absence of the slideable fixation element.

FIGS. 10-12 show an exemplary hip fixation system 160 including a sleeve 78, a nail 54, and a plurality of connecting elements 162 (e.g., struts) each extending from sleeve 78 to nail 54. Sleeve 78, nail 54, and connecting elements 162 all may be formed integrally with one another. Each of the connecting elements 162 is reversibly deformable. Accordingly, the connecting elements collectively form a compliant member 80 and at least part of a compliant interface 82. The connecting elements may each extend separately from a wall of aperture 70 to sleeve 78, or at least a subset of the connecting elements may join one another intermediate the wall and sleeve 78. Each connecting element 162 may extend along a nonlinear path (e.g., a curved path) between the wall of aperture 70 and sleeve 78. The nonlinear path may turn and/or reverse direction one or more times. Each connecting element 162 may extend from a lower or bottom wall region of aperture 70 or from an upper or top wall region of aperture 70. Alternatively, one or more connecting elements may extend to sleeve from a side wall region of aperture 70 that is intermediate the top and bottom wall regions of the aperture. The connecting elements may be flanked by openings 164 that permit the connecting elements to move relative to one another. The connecting elements may deform as fixation element 56 changes its angular orientation with respect to the nail, and may bind on one another to limit changes to the angular orientation and to increase resistance to further changes to the angular orientation.

Nail 54, sleeve 78, and connecting elements 162 may be cast or molded or may be formed from a one-piece precursor by removing material, such as by electrical discharge machining, laser machining, chemical etching, or the like.

Figure 13:
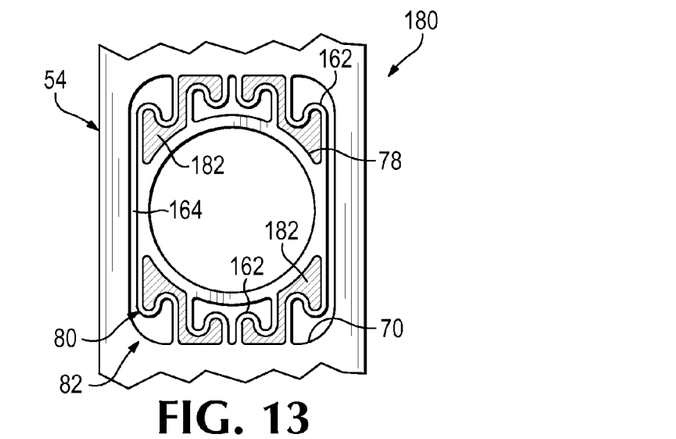
FIG. 13 is a fragmentary elevation view of a modified form of the hip fixation system of FIG. 10, taken generally as in FIG. 11, and having a compliant material disposed between deformable connecting elements of the compliant member.

FIG. 13 shows a hip fixation system 180 that is a modified version of hip fixation system 160 (also see FIGS. 10-12). More particularly, a deformable material (e.g., an elastomer) has been placed into a subset of openings 164 to create deformable elements 182 between pairs of connecting elements 162. Deformable elements 182 may molded in situ or may be formed separately and then inserted into openings 164.

Figure 14:
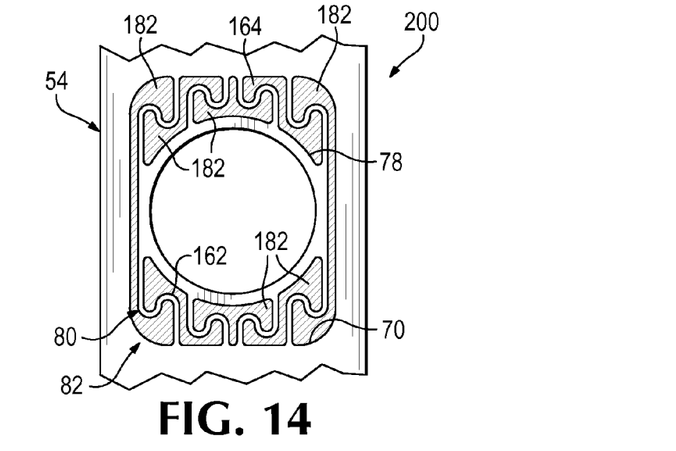
FIG. 14 is a fragmentary elevation view of another modified form of the hip fixation system of FIG. 10, taken generally as in FIG. 11, and having a compliant material disposed in each opening that is intermediate the sleeve and the nail.

FIG. 14 shows another hip fixation system 200 that is a modified version of hip fixation system 160 (also see FIGS. 10-12). In the depicted embodiment, a deformable element 182 fills each opening 164.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A system for hip fixation, comprising:
   an intramedullary nail configured to be placed longitudinally into a proximal femur of a subject;
   a sleeve disposed in the nail;
   a fixation element configured to be placed into the proximal femur and through the sleeve, such that the fixation element is slideable along its long axis in the sleeve and extends out of the nail to a head of the proximal femur and is anchored in the head; and
   a compliant member located in the nail and configured to deform reversibly in response to a load applied to the head of the proximal femur by the subject after the nail and the fixation member have been implanted in the proximal femur of the subject, to reversibly change an angular orientation of the fixation element with respect to the nail;
   wherein the angular orientation is defined as an angle formed between a long axis of the nail and the long axis of the fixation element.

2. The system of claim 1, wherein the compliant member includes an elastomer.

3. The system of claim 2, wherein the elastomer is viscoelastic.

4. The system of claim 1, wherein the sleeve and the nail are formed separately from one another.

5. The system of claim 4, wherein the sleeve and the compliant member are formed of different materials relative to one another.

6. The system of claim 5, wherein the sleeve is formed of metal and the compliant member includes a polymer.

7. The system of claim 4, wherein the compliant member is formed in situ between the nail and the sleeve.

8. The system of claim 4, wherein the compliant member and the sleeve have complementary surface features that restrict movement of the compliant member and the sleeve relative to one another.

9. The system of claim 1, wherein the nail defines an aperture, and wherein at least a portion of the compliant member is disposed between the sleeve and a wall of the aperture.

10. The system of claim 1, wherein the nail defines an aperture in which the compliant member is mounted.

11. The system of claim 10, wherein the compliant member and a wall of the aperture have complementary surface features that restrict removal of the compliant member from the aperture.

12. The system of claim 1, wherein the compliant member includes a pair of deformable elements that are formed separately from one another.

13. The system of claim 1, wherein the compliant member includes a spring.

14. The system of claim 1, wherein at least a portion of the compliant member is continuous with the nail.

15. The system of claim 1, wherein the fixation element has an external thread to anchor the fixation element in the head of the femur.

16. A method of hip fixation, the method comprising, in any order:
    placing an intramedullary nail longitudinally in a proximal femur of a subject, the nail containing a sleeve; and
    placing a fixation element into the proximal femur and through the sleeve, such that the fixation element is slideable along its long axis in the sleeve and extends out of the nail to a head of the proximal femur and is anchored in the head;
    wherein a compliant member is located in the nail and is configured to deform reversibly in response to a load applied to the head of the proximal femur by the subject, to reversibly change an angular orientation of the fixation element with respect to the nail, and
    wherein the angular orientation is defined as an angle formed between a long axis of the nail and the long axis of the fixation element.

17. The method of claim 16, further comprising a step of selecting the compliant member based on one or more characteristics of the subject, wherein the compliant member is selected from a set of two or more compliant members having different deformabilities relative to one another.

18. The method of claim 17, wherein the set of two or more different compliant members are provided by a set of two or more nails each containing one of the two or more different compliant members.

19. A system for hip fixation, comprising:
    an intramedullary nail configured to be placed longitudinally into a proximal femur of a subject;
    a fixation element configured to be placed into the proximal femur and transversely through the nail, such that the fixation element is slideable along its long axis in the nail and extends out of the nail to a head of the proximal femur and is anchored in the head; and
    a compliant member located in the nail and configured to deform reversibly in response to a load applied to the head of the proximal femur by the subject after the nail and the fixation member have been implanted in the proximal femur of the subject, to reversibly change an angular orientation of the fixation element with respect to the nail;
    wherein the angular orientation is defined as an angle formed between a long axis of the nail and the long axis of the fixation element, and
    wherein the compliant member is formed of material selected from the group consisting of (a) metal and (b) a composite including a polymer matrix containing carbon fibers.

* * * * *